United States Patent
Hennessy et al.

[11] Patent Number: 5,840,718
[45] Date of Patent: Nov. 24, 1998

[54] 22-EPIMERIC-1,25-DIHYDROXY-16,22,23-TRIENE-CHOLECALCIFEROL

[75] Inventors: Bernard Michael Hennessy, Nutley; Jerome Anthony Iacobelli, Paramus; Milan Radoje Uskokovic, Upper Montclair, all of N.J.

[73] Assignee: Hoffmann-La Roche Inc., Nutley, N.J.

[21] Appl. No.: 811,809

[22] Filed: Mar. 6, 1997

[51] Int. Cl.⁶ .................................................. A61K 31/59
[52] U.S. Cl. ........................ 514/167; 552/653; 556/489; 556/482
[58] Field of Search ............... 552/653; 556/489, 556/482; 514/167

[56] References Cited

U.S. PATENT DOCUMENTS

| | | | |
|---|---|---|---|
| 5,087,619 | 2/1992 | Baggiolini .................. | 514/167 |
| 5,384,314 | 1/1995 | Doran et al. ................ | 514/167 |
| 5,612,328 | 3/1997 | Baggiolini et al. ........... | 514/167 |

OTHER PUBLICATIONS

A.S. Craig, A.W. Norman, W.H. Okamura, J. Org. Chem. 57, pp. 4374–4380 (1992).

*Primary Examiner*—James H. Reamer
*Attorney, Agent, or Firm*—George W. Johnston; Dennis P. Tramaloni; Joseph P. Kirk, Jr.

[57] ABSTRACT

The invention relates to a compound of the formula

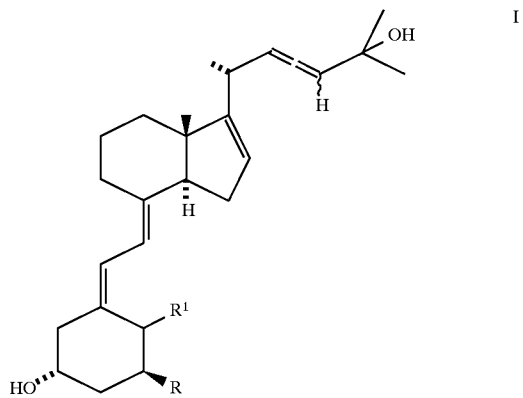

wherein R is hydroxy and $R^1$ is $H_2$ or $=CH_2$ or R is hydrogen or fluoro and $R^1$ is $=CH_2$ and (b) an inert carrier.

Compounds of formula I are useful as agents for the treatment of hyperproliferative skin diseases, such as psoriasis, neoplastic diseases, such as leukemia, and sebaceous gland diseases, such as acne and sebhorreic dermatitis.

16 Claims, No Drawings

22-EPIMERIC-1,25-DIHYDROXY-16,22,23-TRIENE-CHOLECALCIFEROL

This is a provisional Ser. No. 60/023809 filed Mar. 21, 1996.

BRIEF SUMMARY OF THE INVENTION

The invention relates to a compound of the formula

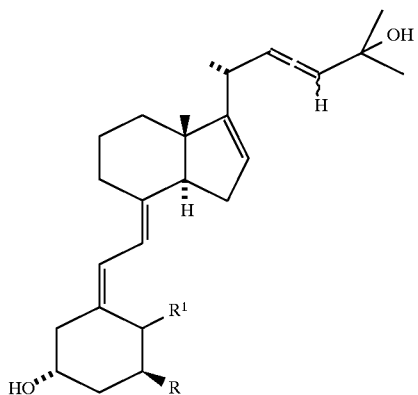

wherein R is hydroxy and $R^1$ is $H_2$ or $=CH_2$ or R is hydrogen or fluoro and $R^1$ is $=CH_2$.

Compounds of formula I are useful as agents for the treatment of hyperproliferative skin diseases, such as, psoriasis. Compounds of formula I as described above are also useful as agents for the treatment and prevention of neoplastic diseases, such as leukemia. Compounds of formula I are also useful as agents for the treatment of sebaceous gland diseases, such as, acne and sebhorreic dermatitis. Compounds of formula I are also useful as agents for the treatment of diseases which require modulation of the immune system, such as transplant rejection, graft vs. host diseases, and the like.

DETAILED DESCRIPTION OF THE INVENTION

As used herein, the term "lower alkyl" denotes a straight or branched-chain alkyl croup containing 1 to 4 carbon atoms, for example, methyl, ethyl, propyl, isopropyl, butyl, t-butyl and the like. The term "ar-lower alkyl" are p-tolyl, benzyl, phenylethyl, phenylpropyl, and the like. The term "aryl" denotes a group derived from an aromatic hydrocarbon which may be unsubstituted or substituted by one or more lower alkyl groups. Exemplary of "aryl" are phenyl and p-methyl phenyl.

In the formulas presented herein, the various substituents are illustrated as joined to the nucleus by one of the following notations: a wedged solid line

◀ indicating a substituent which is above the plane of the molecule (β-orientation), and a wedged dotted line

........

indicating a substituent which is below the plane of the molecules (α-orientation).

The invention relates to a compound of the formula

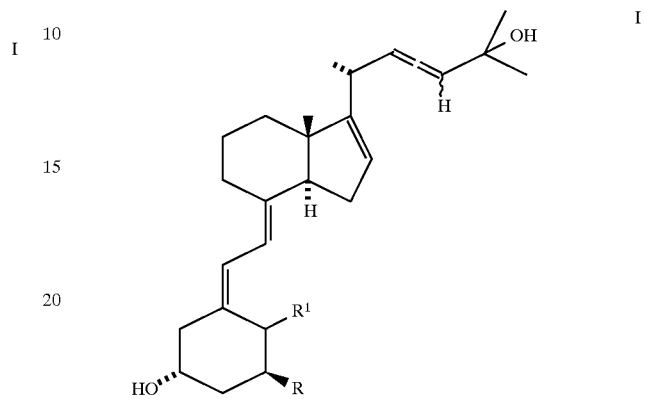

wherein R is hydroxy and $R^1$ is $H_2$ or $=CH_2$ or R is hydrogen or fluoro and $R^1$ is $=CH_2$.

Compounds of formula I as described above are useful as agents in the treatment of hyperproliferative skin disorders such as psoriasis. The compounds of formula I are also useful as agents in the treatment of neoplastic diseases such as leukemia. The compounds of formula I are also useful as agents in the treatment of sebaceous gland diseases, such as acne and sebhorreic dermatitis. Compounds of formula I are also useful as agents in the treatment of diseases which require modulation of the immune system, such as transplant rejection, graft vs. host diseases, and the like.

The invention relates to a composition comprising a compound of formula I, or a mixture of two or more compounds of formula I.

The invention relates to a composition comprising a compound of formula I, or a mixture of two or more compounds of formula I.

The invention also relates to a method for treating the above-mentioned disease states by administration of a compound of formula I, or a mixture of two or more compounds of formula I.

The invention also relates to a process for preparing compounds of formula I. The invention also relates to intermediates of formulas IX, X, VIa, VIb, II, III, XI, and XII described below.

In a preferred embodiment of the compounds of formula I, R is hydroxy and $R^1$ is $=CH_2$. In another compound of formula I, $R^1$ is $H_2$.

Most preferred compounds of formula I are:
1,25-dihydroxy-16,22S,23-triene-cholecalciferol;
1,25-dihydroxy-16,22R,24-triene-cholecalciferol;

The 22S epimer of the compounds of formula I are prepared as hereafter described, with particular reference to Formula Schemes I–III and the Examples below.

FORMULA SCHEME I

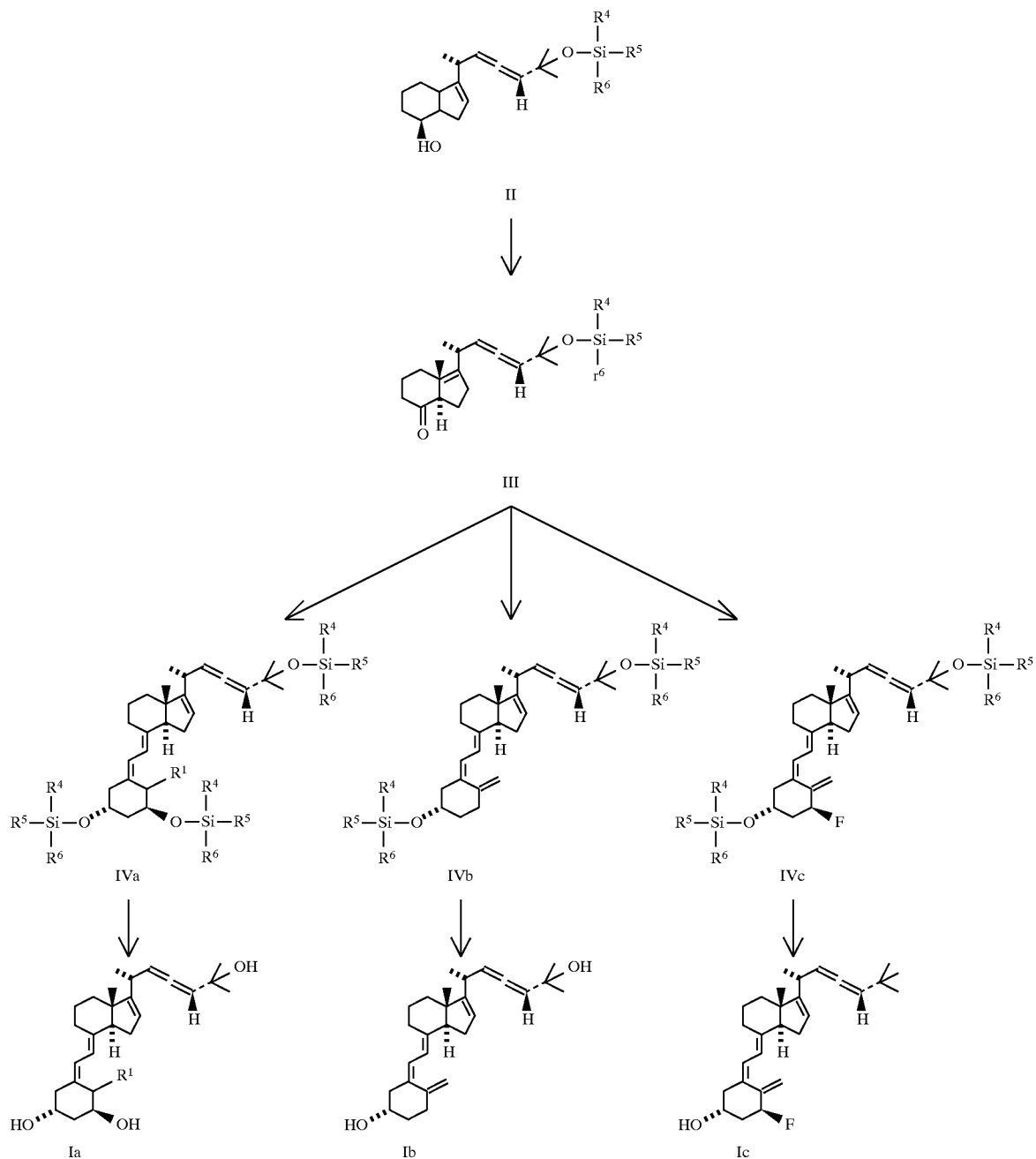

wherein $R^1$ is as described above and $R^4$ and $R^6$ are independently lower alkyl and $R^5$ is independently lower alkyl, aryl, or ar-lower alkyl.

In the above Formula Scheme I, a compound of formula II is oxidized to a compound of formula III by treatment with an oxidizing agent such as 2,2'-bipyridinium chloromate, or pyridinium dichromate, at room temperature, in an aprotic solvent such as dry tetrahydrofuran, or more preferably, dry methylene chloride.

The resulting compound of formula III is converted to a compound of formula IVa, IVb, or IVc by reaction with the corresponding compound of formula

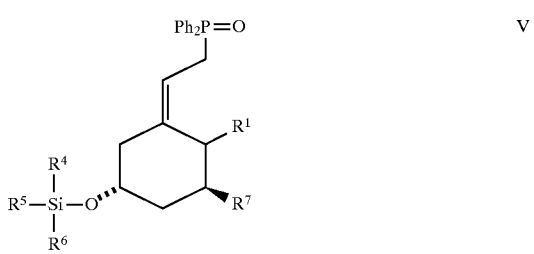

where Ph is phenyl; and $R^1$, $R^4$, $R^5$ and $R^6$ are as described above; $R^7$ is hydrogen, fluorine or

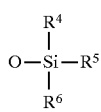

wherein $R^4$, $R^5$ and $R^6$ are as described above.

The reaction is carried out at −60° C. to −90° C., preferably −78° C., in a polar, aprotic, organic solvent, such as dry ether or more preferably dry tetrahydrofuran, in the presence of a strong base such as an alkyl lithium like butyl lithium.

Compounds of formula V are known or can be prepared in accordance with known methods.

The protecting groups of a compound of formula IVa, IVb or IVc are removed by reaction with a fluorine salt, such as tetrabutyl-ammonium fluoride in an organic solvent such as ether, or more preferably tetrahydrofuran to yield a corresponding compound of formula Ia, Ib or Ic.

The intermediates of formula II as described above are prepared as hereinafter described with particular reference to Formula Scheme II and the Examples below.

FORMULA SCHEME II

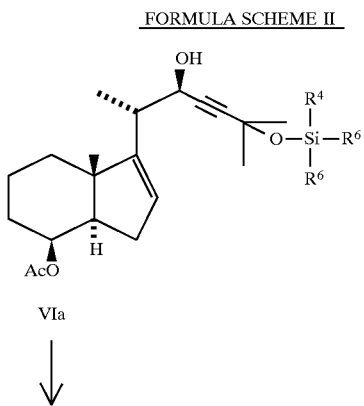

VIa

-continued
FORMULA SCHEME II

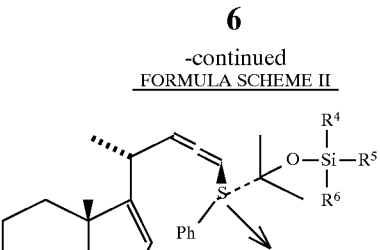

VII

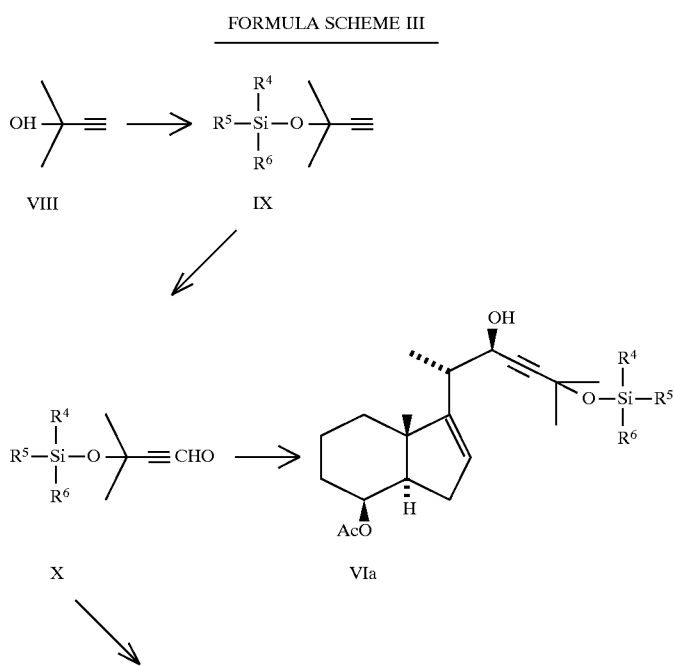

II wherein $R^4$, $R^5$ and $R^6$ are as described above.

In the above formula Scheme II, a compound of formula VIa is converted to a compound of formula VII by reaction with phenyl sulfenyl chloride and triethylamine.

A compound of formula VII is converted to a compound of formula II by reaction with methanol and tert.butyl-lithium.

The intermediates of formula VIa as described above are prepared as hereinafter described with particular reference to Formula Scheme III and the Examples below.

FORMULA SCHEME III

-continued
FORMULA SCHEME III

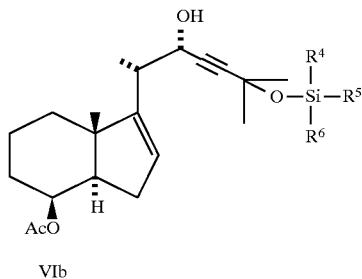

VIb wherein $R^4$, $R^5$, and $R^6$ are as described above.

In the above Formula Scheme III, a compound of formula VIII, which is known, is converted to a compound of formula IX by reaction with a trialkylsilyl chloride such as t.butyldimethylsilyl chloride in the presence of a base such as imidazole and in the presence of an aprotic organic solvent such as dry N,N-dimethylformamide.

A compound of formula IX is converted to a compound of formula X by reaction with a base, such as n-butyllithium and N,N-dimethylformamide, in anhydrous tetrahydrofuran as solvent, preferably at −78° C.

A compound of formula X is reacted with [3aR-Z,3aα, 4β,7aβ]-1-ethylidene-octahydro-7a-methyl-1H-4-indenol acetate and dimethylaluminum chloride as Lewis acid in chlorinated hydrocarbon solvent, such as methylene chloride, preferably at a temperature of −78° C. The resulting compound is treated to separate its epimers, providing a compound of formulas VIa and a compound of formula VIb.

The 22R epimer compounds of formula I are prepared as hereafter described, with particular reference to Formula Schemes IV-V and the Examples below.

FORMULA SCHEME IV

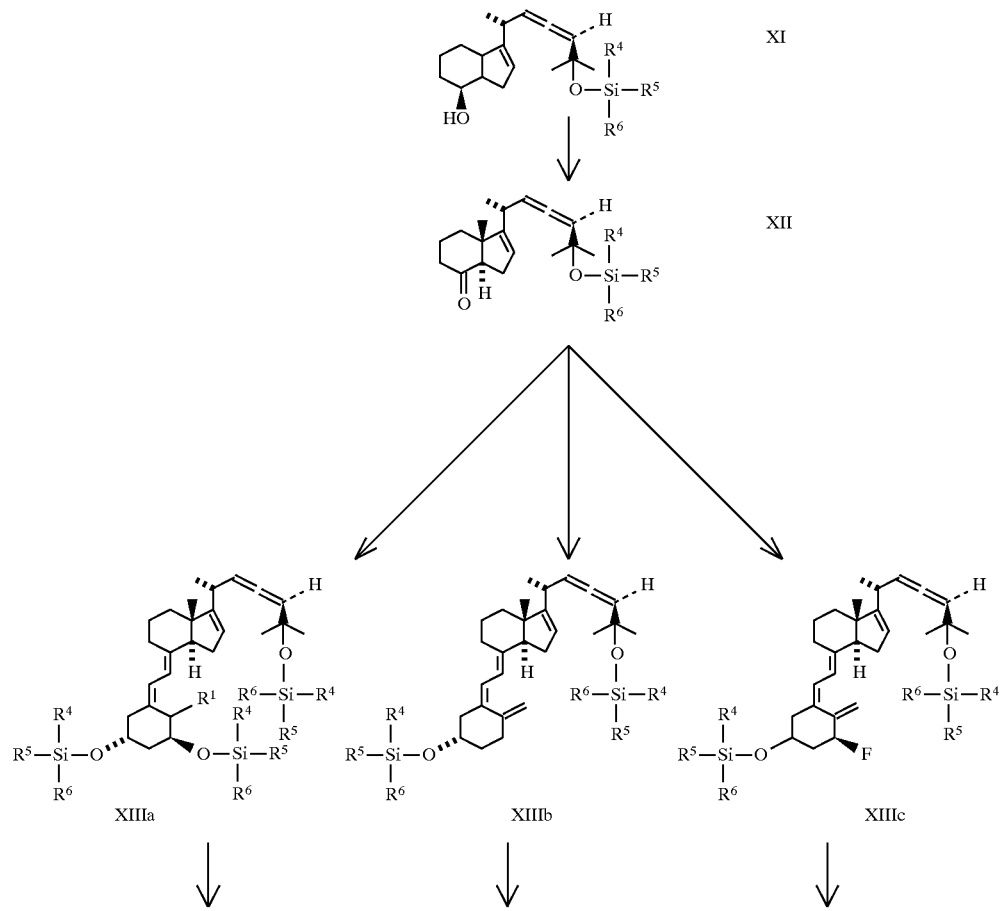

-continued
FORMULA SCHEME IV

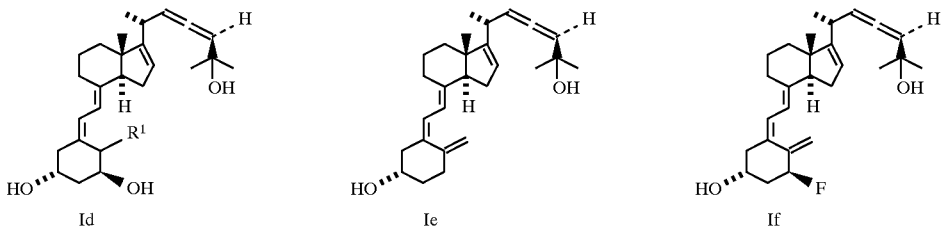

wherein $R^1$, $R^4$, $R^5$ and $R^6$ are as described above.

In the above Formula Scheme IV, a compound of formula XI is oxidized to a compound of formula XII by treatment with an oxidizing agent such as 2,2'-bipyridinium chloromate, or pyridinium dichloromate, at room temperature, in an aprotic solvent such as dry tetrahydrofuran, or more preferably, dry methylene chloride.

The resulting compound of formula XII is converted to a compound of formula XIIIa, XIIIb, or XIIIc by reaction with the corresponding compound of formula

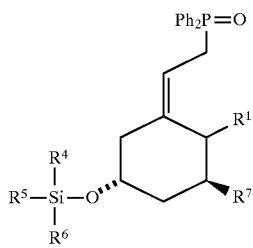

where Ph, $R^1$, $R^4$, $R^5$, $R^6$ and $R^7$ are as described above.

The reaction is carried out at −60° C. to −90° C., preferably −78° C., in a polar, aprotic, organic solvent, such as dry ether or more preferably dry tetrahydrofuran in the presence of a strong base such as an alkyl lithium like butyl lithium.

The protecting groups of a compound of formula XIIIa, XIIIb or XIIIc are removed by reaction with a fluorine salt, such as tetrabutyl-ammonium fluoride in a polar, organic solvent such as ether, or more preferably tetrahydrofuran to yield a corresponding compound of formula Id, Ie or If.

The intermediates of formula XI as described above are prepared as hereinafter described with particular reference to Formula Scheme V and the Examples below.

FORMULA SCHEME V

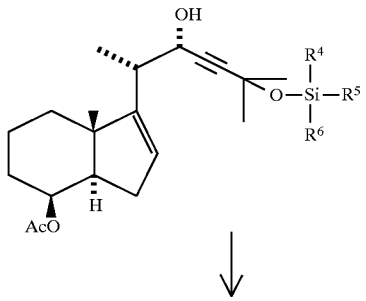

-continued
FORMULA SCHEME V wherein $R^4$, $R^5$ and $R^6$ are as described above.

In the above Formula Scheme V, a compound of formula VIb is converted to a compound of formula XIV by reaction with phenyl sulfenyl chloride and triethylamine.

A compound of formula XIV is converted to a compound of formula XI by reaction with methanol and tert.butyl-lithium.

The intermediates of formula VIb as described above are prepared as described with particular reference to Formula Scheme III above and the Examples below.

The compounds of formula I as described above can be administered orally, for the treatment of hyperproliferative skin diseases such as psoriasis, basal cell carcinomas, disorders of keritination, and keratosis, to warmblooded animals which need such treatment. More specifically, the compounds of formula I as described above can be administered orally to an adult human in dosages that are in the range of about 0.5 to 50 μg per day for the treatment of hyperproliferative skin diseases such as psoriasis, basal cell carcinomas, disorders of keratinization, and keratosis.

The compounds of formula I as described above can be administered orally, for the treatment of neoplastic diseases such as leukemia, to warmblooded animals which need such treatment. More specifically, the compounds of formula I as described above can be administered orally to an adult human in dosages that are in the range of about 0.5 to 50 μg per day for the treatment of neoplastic diseases such as leukemia.

The compounds of formula I as described above can be administered orally for the treatment of sebaceous gland diseases, such as acne or sebhorreic dermatitis, to warmblooded animals in need of such treatment. More specifically, the compounds of formula I as described above can be administered orally to an adult human in dosages that are in the range of about 0.5 to 50 µg per day for the treatment of sebaceous gland diseases, such as acne or sebhorreic dermatitis.

The compounds of formula I as described above can be administered orally for the treatment of diseases which require modulation of the immune system, such as transplant rejection, graft vs. host disease, and the like, to warm-blooded animals in need of such treatment. More specifically, the compounds of formula I as described above can be administered orally to an adult human in dosages that are in the range of 0.5 to 50 µg per day for the treatment of diseases which require modulation of the immune system, such as transplant rejection, graft vs. host disease, and the like.

The compounds of formula I as described above can be administered topically, for the treatment of hyperproliferative skin diseases such as psoriasis, to warmblooded animals which need such treatment. More specifically, the compounds of formula I as described above can be administered topically in dosages that are in the range of about 0.5 to 50 µg per gram of topical formulation per day, for the treatment of hyperproliferative skin diseases such as psoriasis, basal cell carcinomas, disorders of keratinization, and keratosis.

The compounds of formula I as described above can be administered topically, for the treatment of sebaceous gland diseases such as acne or sebhorreic dermatitis, to warm-blooded animals which need such treatment. More specifically, the compounds of formula I as described above can be administered topically in dosages that are in the range of about 0.5 to 50 µg per gram of topical formulation per day, for the treatment of sebaceous gland diseases, such as acne or sebhorreic dermatitis.

The dosage of the compounds of formula I can vary within wide limits depending on the illness to be treated, the age and the individual condition of the patient and on the mode of administration and will, of course, be fitted to the individual requirements in each particular case.

The useful activity of compounds of formula I as agents for the treatment of hyperproliferative skin disease can be demonstrated by the following.

Inhibition of Keratinocyte Proliferation

HaCaT cell line—The immortalized human cell line HaCaT was used (originally obtained from N. E. Fusenig, German Cancer Research Center, Heidelberg, Germany). $^3$H-thymidine incorporation was measured in exponentially growing cultures after 6 days of culture in presence of the test compound.

Cell culture—HaCaT cells were cultured in a mixture of Dulbecco's Modified Eagle Medium containing 4.5 g glucose and Nutrient Mixture Ham's F12, 3:1 (v/v). This mixture was supplemented with 10% fetal calf serum (FCS), 2 mM L-glutamine, 50 UI/ml, penicillin, 50 µg/ml streptomycin, 10 ng/ml EGF, 400 ng/ml hydrocortisone, 8.5 ng/ml cholera toxin, and 5 ng/ml insulin. The cells were maintained in a humidified atmosphere containing 5% $CO_2$ and 95% air and passaged every 3–4 days.

Inhibition of $^3$H-thymidine uptake—HaCaT cells (250 cells in 180 µl of the supplemented mixture) were seeded into 96-well culture dishes and incubated at 37° C. with 5% $CO_2$ and 95% air. Immediately after seeding, 20 µl of test compounds listed below in Table II, diluted in the supplemented mixture containing 1% ethanol, were added to the wells to yield final concentrations of between $10^{-9}$ and $10^{-6}$M (starting from 1 mM stock solutions in ethanol, stored at −20° C. and protected from light). After 6 days, $^3$H-thymidine (5 Ci/mmol) was added to the wells at a concentration of 1 µCi/well. Cells were pulse-labeled for the last 6 hours of the growth period. Cells were then trypsinized for 10 minutes at 37° C. under a vigorous agitation and harvested on to a 96-well filter plate using a cell harvester. After drying at 40° C. under vacuum for 20–30 minutes, 20 µl of scintillator was added and the radioactivity bound to the filters was counted.

Values are expressed as percent of controls (samples without test compound). The concentration leading to 50% of control values is determined graphically and given as $IC_{50}$ (inhibitory concentration) in Table I.

TABLE I

| COMPOUND | $IC_{50}$ (nM) |
| --- | --- |
| 1,25-Dihydroxy-cholecalciferol | 55.0 |
| 1,25-Dihydroxy-16,22S,23-triene-cholecalciferol | 40.0 |
| 1,25-Dihydroxy-16,22R,23-triene-cholecalciferol | 0.01 |

From the above results, it can be seen that compounds of formula I inhibit proliferation of keratinocytes. Accordingly, compounds of formula I are useful in the treatment of hyperproliferative skin diseases, such as psoriasis.

The useful activity of compounds of formula I as agents for the treatment of neoplastic diseases can be demonstrated by the following test procedures.

Induction of HL-60 Cell Differentiation

The induction of differentiation of HL-60 cells was assayed by measuring their oxidative burst potential via the reduction of nitrobluetetrazolium (NBT).

HL-60 cells were maintained in RPMI 1640 medium supplemented with 10% FCS, 2 mM L-glutamine, 1 mM sodium pyruvate, 1% non-essential amino acids, 50 U/ml penicillin, and 50 µg/ml streptomycin. HL-60 cells (30,000 cells in 90 µl of supplemented RPMI medium) were seeded into flat-bottomed microliter wells. Immediately after seeding, 10 µl of test compounds listed below in Table II diluted in supplemented RPMI medium were added to the wells to yield final concentrations of between $10^{-11}$ and $10^{-6}$M (starting from stock solutions of $10^{-2}$M in ethanol, stored at −20° C. and protected from light). After 3 days, medium was removed from the wells with a multichannel pipette and replaced with 100 µl of NBT solution (1 mg/ml in phosphate buffered saline with 200 nM phorbol myristate acetate). Following an additional hour incubation at 37° C. the NBT solution was removed and 100 µl of 10% sodium dodecyl sulfate in 0.01N HCl was added. The amount of the reduced NBT was quantified photometrically at 540 nm using an automated plate reader. The mean of 3 wells was calculated. S.E.M. were between 5 and 10%. Values were expressed as percent of maximal differentiation achieved with 100–1000 nM calcitriol in the same experiment. The concentration (nM) leading to 50% of this maximal value is determined graphically and given in Table II as $ED_{50}$.

TABLE II

| COMPOUND | $ED_{50}$ (nM) |
| --- | --- |
| 1,25-Dihydroxy-cholecalciferol | 6.0 |
| 1,25-Dihydroxy-16,22S,23-triene-cholecalciferol | 4.8 |
| 1,25-Dihydroxy-16,22R,23-triene-cholecalciferol | 0.22 |

From the above results, it can be seen that compounds of formula I induce differentiation of HL-60 cells and thereby stop these tumor cells from growing. Accordingly, compounds of formula I are useful in the treatment of neoplastic diseases such as leukemia.

The useful activity of compounds of formula I as agents for the treatment of sebaceous gland diseases, such as acne and sebhorreic dermatitis, can be demonstrated by the following test procedure.

Inhibition of Sebaceous Cell Proliferation

Sebaceous cells were isolated from adult human sebaceous glands, derived from facial skin removed during cosmetic surgery. This method is described in an article by Doran et al. in *J. Invest. Dermatol.* 96:341–348 (1991).

The cells were cultured in Iscove's medium containing 10% fetal calf-serum and 4 μg/ml dexamethasone on a layer of growth-arrested 3T3 mouse fibroblasts.

Cells were plated in medium without the test compound and then given the compound in fresh medium 24–48 hours after the initial plating. The cultures were given fresh medium, containing the test compound, every 48 hours. On the day of harvesting, the cultures were rinsed with 0.03% ethylenediamine tetraacetic acid (EDTA) in phosphate buffered saline (PBS), to remove only the 3T3 fibroblasts. The remaining sebocyte colonies were incubated in 0.05% trypsin/0/03% EDTA to create a single cell suspension of sebocytes. The cells were suspended, mixed vigorously to prepare a single cell suspension, and counted in a hemocytometer.

All compounds were handled in the following manner. Stock solutions were made up as $10^{-2}$M solutions in degassed 100% ethanol and stored at $-20°$ C. in the dark. Solutions were never used after storage of more than a month. During experimental use the solutions, which had been aliquoted, were thawed once and used by diluting directly into complete medium to the appropriate concentration.

The compounds were tested for the inhibition of proliferation of sebaceous cells in vitro at the following concentrations: $10^{-8}$, $10^{-7}$ and $10^{-6}$M.

The results are summarized in Table III below as the amount of compound necessary to inhibit the proliferation of the sebaceous cells by 50% ($ED_{50}$) in μM as compared to a control, vehicle treated only, culture.

TABLE III

| COMPOUND | $ED_{50}$ (μM) |
| --- | --- |
| 1,25-Dihydroxy-cholecalciferol | 0.05 |
| 1α,25-Dihydroxy-16,22S,23-triene-cholecalciferol | 0.01 |
| 1α,25-Dihydroxy-16,22R,23-triene-cholecalciferol | 0.001 |

From the above results, it can be seen that the compounds of formula I inhibit sebaceous cell proliferation. Accordingly, the compounds of formula I are useful in the treatment of sebaceous gland diseases such as acne and sebhorreic dermatitis.

The useful activity of compounds of formula I as agents for the treatment of diseases which require modulation of the immune system can be demonstrated by the following.

Inhibition of γ-Interferon Release in Human T-cells

Mononuclear cells were isolated from venous blood of healthy donors by centrifugation of buffy coat leucocytes atop Ficoll-Paque. The lymphocytes (70–80% T-cells) were suspended in RPMI 1640 medium supplemented with 10% FCS and adjusted to $10^6$ cells/ml. 100 μl of this cell suspension were seeded into flat-bottom microtiter wells and stimulated with 1 μg/ml of the T-cell specific mitogen phytohemagglutinine (PHA). Immediately after seeding, the test compounds listed below in Table IV were added to yield final concentrations of between $1\times10^{-11}$M–$1\times10^{-6}$M. All tests were run in the quadruplicates.

On days 3 and 4, medium was removed from the wells and the content of IFN-γ was analyzed by ELISA. Values are expressed as percent of controls (samples without test compound). The concentration leading to 50% of control values is determined graphically and given as $IC_{50}$ (inhibitory concentration) in Table IV.

TABLE IV

| COMPOUND | $IC_{50}$ (nM) |
| --- | --- |
| 1,25-Dihydroxy-cholecalciferol | 0.8 |
| 1,25-Dihydroxy-16,22S,23-triene-cholecalciferol | 3 |
| 1,25-Dihydroxy-16,22R,23-triene-cholecalciferol | 0.05 |

Inhibition of Human T-cell Proliferation

Mononuclear cells were isolated from venous blood of healthy donors by centrifugation of buffy coat leucocytes atop Ficoll-Paque. The lymphocytes (70–80% T-cells) were suspended in RPMI 1640 medium supplemented with 10% FCS and adjusted to $10^6$ cells/ml. 100 ml of this cell suspension were seeded into flat-bottom microtiter wells and stimulated with 1 mg/ml of PHA. Immediately after seeding, the test compounds listed below in Table V were added to yield final concentrations of between $1\times10^{-11}$M–$1\times10^{-6}$M. All tests were run in the quadruplicates.

After 3 and 4 days, $^3$H-thymidine (5 Ci/mmol) was added to wells at a concentration of 1 mCi/well. Cells were pulse-labeled for the last 6 hours of the growth period. Cells were then harvested on to a 96 well filter plate using a cell harvester. After drying at 40° C. under vacuum for 20–30 minutes, 20 μl of scintillor were added and the radioactivity bound to the filters was counted. Values are expressed as percent controls (samples without test compounds). The concentration leading to 50% of control values is determined graphically and given as $IC_{50}$ (inhibiting concentration) in Table V.

TABLE V

| COMPOUND | $IC_{50}$ (nM) |
| --- | --- |
| 1,25-Dihydroxy-cholecalciferol | 10.0 |
| 1,25-Dihydroxy-16,22S,23-triene-cholecalciferol | 6.0 |
| 1,25-Dihydroxy-16,22R,23-triene-cholecalciferol | 0.55 |

From the above results, it can be seen that compounds of formula I inhibit γ-interferon release in human T-cells and inhibit human T-cell proliferation. Accordingly, compounds of formula I are useful in the treatment of diseases which require modulation of the immune system, such as transplant rejection, graft vs. host disease, and the like.

Calcium tolerance test in mice

Profound changes in calcium homeostasis strongly affect the weight development of mice.

Mice (25–30 g body weight) received daily subcutaneous administrations of the compound for 4 consecutive days. Body weight was registered just before and at the end of a 5 day treatment period. The "highest tolerated dose" (HTD) is the dose which results in zero weight gain during this treatment period. The results are set forth in Table VI.

TABLE VI

| COMPOUND | HTD ($\mu$g/kg) |
|---|---|
| 1,25-Dihydroxycholecalciferol | 0.5 |
| 1,25-Dihydroxy-16,22S,23-triene-cholecalciferol | 50.0 |
| 1,25-Dihydroxy-16,22R,23-triene-cholecalciferol | 2.5 |

From the above results, it can be seen that the compounds of formula I are better tolerated than 1,25-dihydroxycholecalciferol.

Oral dosage forms comprising compounds of formula I of the invention may be incorporated in capsules, tablets and the like with pharmaceutically acceptable carrier materials.

Illustrative of the pharmaceutically acceptable carrier materials which may be incorporated into capsules, and the like are the following: a binder such as gum tragacanth, acacia, corn starch, or gelatin; an excipient such as dicalcium phosphate; a disintegrating agent such as corn starch, potato starch, algenic acid, and the like; a lubricant such as magnesium stearate, a sweetening agent such as sucrose, lactose, or saccharin; a flavoring agent such as peppermint, oil of wintergreen or cherry. Various other materials may be present as coating or to otherwise modify the physical form of the dosage unit. For instance, tablets may be coated with shellac, sugar, or both. A syrup or elixir may contain the active compound, sucrose as a sweetening agent, methyl and propyl parabens as preservatives, a dye, and a flavoring such as cherry or orange flavor.

Topical dosage forms comprising compounds of formula I of the invention include: ointments and creams encompassing formulations having oleaginous, absorbable, water-soluble and emulsion-type bases such as petrolatum, lanolin, polyethylene glycols and the like.

Lotions are liquid preparations and vary from simple solutions to aqueous or hydroalcoholic preparations containing finely divided substances. Lotions can contain suspending or dispersing agents, for example, cellulose derivatives such as ethyl cellulose, methyl cellulose, and the like; gelatin or gums, which incorporate the active ingredient in a vehicle made up of water, alcohol, glycerin and the like.

Gels are semi-solid preparations made by gelling a solution or suspension of the active ingredient in a carrier vehicle. The vehicles, which can be hydrous or anhydrous, are gelled using a gelling agent, such as, carboxy polymethylene, and neutralized to a proper gel consistency with the use of alkalies, such as, sodium hydroxide and amines, such as, polyethylenecocoamine.

As used herein, the term "topical" denotes the use of the active ingredient, incorporated in a suitable pharmaceutical carrier, and applied at the site of the disorder for the exertion of local action. Accordingly, the topical composition include those pharmaceutical forms in which the compound is applied externally by direct contact with the skin. The topical dosage forms comprise gels, creams, lotions, ointments, powders, aerosols and other conventional forms for applying medication to the skin obtained by admixing the compounds of formula I with known pharmaceutical topical carrier materials.

The following Examples are provided to further describe the invention and are not intended to limit it in any way.

EXAMPLE 1
3-Methyl-3-t.butyldimethylsilyloxy-butyne

To the solution of 25 g (0.29 mole) of 3-methyl-3-hydroxy-butyne in 50 ml anhydrous N,N-dimethylformamide was added 44.5 g (0.65 mole) imidazole. After the reaction mixture was cooled in ice bath 50 g (0.33 mole) of t.butyldimethylsilyl chloride was added. The reaction mixture was stirred in ice-bath for 15 minutes and at RT overnight. 250 mg of dimethylaminopyridine was then added and heated for two hours at 70° C. The reaction mixture was poured in 1 liter of cold water and extracted with 5×150 ml of ether. The ether extract was washed with water and brine, dried over magnesium sulfate and evaporated to dryness. Purification was performed by FLASH chromatography on silica-gel column with pentane, and distillation under house vacuum (b.p. 120° C.) to give 31.81 g (54%) of the title compound. $^1$H-NMR (CDCl$_3$):δ0.87 (s, 9H), 1.47 (s, 6H), 2.39 (s, 1H). Analysis: Calcd for $C_{11}H_{22}OSi$: C 66.60, H 11.18; Found: C. 66.13, H 11.46.

EXAMPLE 2
4-Methyl-4-t.butyldimethylsilyloxy-butynal

To the solution of 10 g (50 mmole) of 3-methyl-3-t.butyl-dimethyl-silyloxy-butyne in 25 ml of anhydrous tetrahydrofurane cooled to −78° C. was added dropwise over a 40 minute period 40 ml (63 mmole) 1.6M n-butyllithium in hexane. After stirring for 1 hour at −78° C., 31 ml (400 mmole) of N,N-dimethylformamide was added dropwise, and the stirring was continued for ½ hour. The reaction mixture was then poured in 300 ml water and brine, and extracted with 4×75 ml pentane. The extracts were washed with ammonium chloride solution, water and brine, dried over sodium sulfate, and evaporated to dryness. Purification was done by distillation to give 8.88 g (78%) of title compound, b.p. 92°–94° C. at 8 mm Hg. $^1$H-NMR (CDCl$_3$): δ0.87 (s, 9H), 1.54 (s, 6H), 9.24 (s, 1H).

EXAMPLE 3
Epimeric mixture 3aR-[1(R*),3aα,4β,7αβ]-3,3a,5,6,7,7a-hexahydro-7a-methyl-1[2(R,S)-hydroxy-5-(tert.butyl-dimethylsilyloxy)-1,5-dimethyl-3-hexynyl]-4H-indenol acetate To the solution of 2 g (9 mmole) of [3aR-Z,3aα,4β,7αβ]-1-ethylidene-octahydro-7a-methyl-1H-4-indenol acetate and 2.25 g (9 mmole) of 4-methyl-4-tert.butyl-dimethylsilyloxy-butynal in 5 ml anhydrous methylene chloride cooled at −78° C. was added over a 10 minute period 20 ml (20 mmole) 1M solution of dimethyl aluminum chloride. Since after two hours the reaction by TLC was only half complete, additional 2.25 g of aldehyde and 20 ml of dimethyl aluminum chloride were added. The reaction was complete after 1 hour additional stirring. It was poured into 600 ml 2N potassium bicarbonate, extracted with 4×100 ml ethyl acetate; extracts were washed with water and brine, dried over sodium sulfate and evaporated to dryness. The FLASH chromatography on a silica gel column first with methylene chloride and then hexane-ethyl acetate (3:1) gave 4.16 g (100%) of the title epimeric mixture. Separation of epimers was accomplished by HPLC with hexane-ethylacetate 10:1 to give 3.25 g (78%) of the 2R-epimer, m.p. 47°–48° C.; $[\alpha]_D^{25}$+7.20° (c 0.555 EtOH); $^1$H-NMR (CDCl$_3$): δ0.15 (s, 3H, SiCH$_3$), 0.16 (s, 3H, SiCH$_3$), 0.86 (s, 9H, SitBu), 1.04 (s, 3H, CH$_3$), 1.14 (d, 3H, J=6.9 Hz, CH$_3$), 1.44 (s, 6H, 2CH$_3$), 2.05 (s, 3H, CH$_3$CO), 2.40 (p, 1H, J=6.4 Hz, CH), 4.43 (t, 1H, J=6.3 Hz, CH), 5.21 (brs, 1H, CHOAc), 5.68 (brs, 1H, =CH—); Analysis: Calcd for $C_{26}H_{44}O_4$ Si: C 69.59, H 9.88; Found: C 69.85, H 9.74.

And 0.754 g (18%) of the 2S-epimer, m.p. 77°–79° C., $[\alpha]_D^{25}$+18.12° (c 0.524, EtOH); $^1$H-NMR (CDCl$_3$): δ0.17 (2s, 6H, 2SiCH$_3$), 0.87 (s, 9H, Sit.Bu), 1.03 (s, 3H, CH$_3$), 1.14 (d. 3H, J=6.9 Hz, CH$_3$), 1.47 (s, 6H, 2 CH$_3$), 2.05 (s, 3H, CH$_3$ CO), 2.37 (p, 1H, CH), 4.40 (dd, 1H, J=3.7 and 7.8

Hz, CH), 5.21 (brs, 1H, CHOAc), 5.54 (brs, 1H, =CH—); Analysis: Calcd for $C_{26}H_{44}O_4Si$: C 69.59, H 9.88; Found: C 69.42, H 10.15.

EXAMPLE 4

[3aS-[3(1S*,2S*),3aα,7α,7aβ]]-3-[5-[[(1,1-Dimethylethyl) dimethyl-silyl]oxy-1,5-dimethyl-4-(phenylsulfinyl)-2,3-hexadienyl]-3a,4,5,6,7,7a-hexahydro-3α-methyl-1H-inden-7 ol acetate To the solution of 802 mg (1.8 mmole) of [3aS-[3(1R*,2S*), 3aα7α,7aβ]]-7-(acetyloxy)-α-[3[[(1,1-dimethylethyl) dimethylsilyl]oxy-3-methyl-1-butynyl]-3a,4,5,6,7,7a-hexahydro-β,3a-dimethyl-1H-indene-3-ethanol in 20 ml anhydrous ether was added 0.5 ml (3.6 mmole) of triethyl amine. After cooling to −78° C. in a dry-ice bath, 8 ml (4 mmole) of freshly prepared phenyl sulfenyl chloride was added in the course of two hours. The reaction mixture was then diluted with water and extracted with ether. The ether extract was washed with 2N potassium bicarbonate, followed by water till neutral, and brine. After drying over sodium sulfate, the ether solution was evaporated to dryness. The crude product was purified by FLASH chromatography with hexane-ethyl acetate 4:1, and then by preparative HPLC with hexane-ethyl acetate 3:1, to give 878 mg (88.2%) of the title compound as a mixture of two epimeric sulfoxides.

EXAMPLE 5

[3aS-[3(1S*,2R*),3aα,7α,7aβ]]-3-[5-[[(1,1-Dimethylethyl) dimethylsilyl]oxy-1,5-dimethyl-2,3-hexadienyl]-3a,4,5,6,7, 7a-hexahydro,-3a-methyl-1H-inden-7 ol To the solution of 1.68 g (3.02 mmole) of [3aS-[3(1S*, 2S*), 3aα7α,7aβ]]-3-[5[[(1,1-dimethylethyl)dimethylsilyl] oxy]-1,5-dimethyl-4-(phenylsulfinyl)-2,3-hexadienyl]-3a,4, 5,6,7,7a-hexahydro-3α-methyl-1H-inden-7-ol acetate in 550 ml anhydrous ether was added 0.432 ml (11.174 mmole) of anhydrous methanol. Thus obtained mixture was cooled to −100° C. in pentane-liquid nitrogen bath and 10.6 ml (18.12 mmole) of 1.7M tert.butyl lithium was added dropwise in the course of 10 minutes. TLC indicated that the reaction was complete. The reaction was quenched with 8.0 ml methanol and the ether layer was washed with water, then with brine, dried over sodium sulfate and evaporated. The residue was dissolved in 12 ml ethanol and after addition of 7 ml of 2N sodium hydroxide was heated at 70° C. for three hours. The reaction mixture was diluted with water-brine 1:1, extracted with ethyl acetate. The extract was washed with water and brine, dried over sodium sulfate and evaporated to dryness. The crude product was purified by preparative HPLC with hexane-ethyl acetate 7:1. It gave 593 mg (50.25%) of the title compound, which crystallized in freezer, mp 64°–65° C.; $[\alpha]_D^{25}$+99.62° C. (c 0.5, EtOH); $^1$H-NMR (CDCl$_3$): δ0.07 (s, 6H, SiMe$_2$), 0.85 (s, 9H, Si-t.butyl), 1.09 (s, 3H, CH$_3$), 1.11 (d, 3H, J=7 Hz, CH$_3$), 1.29 (s, 3H, CH$_3$), 1.30 (s, 3H, CH$_3$), 1.98, 2.27 (m, 2H, CH$_2$), 2.83 (brm, 1H, CH), 4.18 (brs, 1H, CH), 5.28 (t, 1H, J=6.3 Hz, =CH—), 5.32 (dd, 1H, J=2.8 and 6.3 Hz, =CH—), 5.43 (brs, 1H, =CH—). Analysis: Calcd. for $C_{24}H_{42}O_2Si_2$: C 73.78, H 10.84; Found: C 73.89, H 11.08.

EXAMPLE 6

[3aS-[3(1S*,2R*),3aα,7aβ]]-3-[5-[[(1,1-Dimethyl-ethyl) dimethylsilyl]oxy]-1,5-dimethyl-2,3-hexadienyl]-3a,4,5,6, 7,7a-hexahydro-3a-methyl-1H-inden-7-one A solution of 390 mg (1 mmol) of [3aS-[3(1S*,2R*), 3aα7aβ]]-3-[5-[[(1,1-dimethylethyl)dimethylsilyl]oxy]-1,5-dimethyl-2,3-hexadienyl]-3a,4,5,6,7,7a-hexahydro-3a-methyl-1H-inden-7-ol in 8 ml anhydrous methylene chloride was treated portionwise with 1.694 g (4.5 mmol) of pyridinium dichromate and 85 mg of pyridinium p-toluene sulfonate. This reaction mixture was stirred for 4.5 hours at room temperature. After addition of 20 ml of ether, the mixture was stirred for 20 minutes and then filtered over Celite, and the residue was washed with 3×50 ml of ether. The filtrates were washed with 20 ml ice-cold 1N HCl, water, 40 ml 2N potassium bicarbonate and water-brine mixture. The aqueous layers were extracted with 2×100 ml of ethyl acetate. The combined organic layers were dried over sodium sulfate and evaporated to dryness. The crude product was purified by FLASH chromatography with hexane-ethyl acetate 15:1 to give 350 mg (90%) of the title compound.

EXAMPLE 7

1,25-Dihydroxy-16,22S,23-triene-cholecalciferol

To a solution of 820 mg (0.141 mmole) of [3S-(1Z,3a, 5b)]-2-[3,5-bis[[(1,1-dimethyl)dimethylsilyl]oxy]-2-methylene-cyclohexylidene]-ethyl-di-phenylphosphine oxide in 8 ml anhydrous tetrahydrofuran at −78∞ C. was added dropwise 0.856 ml (1.37 mmole) of 1.6M n-butyllithium in hexane. After stirring for 5 minutes, to thus formed red solution was added a solution of 350 mg (0.9 mmole) of [3aS-[3(1S*,2R*),3aa,7ab]]-3-[5-[[(1,1-dimethylethyl)dimethylsilyl]oxy]-1,5-dimethyl-2,3-hexadienyl]-3a,4,5,6,7,7a-hexahydro-3a-methyl-1H-inden-7-one in 5 ml anhydrous tetrahydrofuran dropwise over a 10 minute period. The reaction was stirred under argon at −78∞ C. for 90 minutes, and then quenched by addition of 10 ml of 1:1 mixture of 2N aqueous potassium sodium tartarate and 2N aqueous KHCO$_3$, and extracted with 3×125 ml ethyl acetate. The organic layers were washed with brine, dried over sodium sulfate and evaporated to dryness. The residue was purified by FLASH chromatography with hexane-ethyl acetate 40:1 to give 475 mg of trisilylated title compound, which was dissolved in 6 ml of anhydrous tetrahydrofuran and treated with 6.4 ml of 1M tetrabutyl ammonium fluoride in tetrahydrofuran under argon. The reaction mixture was stirred for 45.5 hours at room temperature. The reaction was quenched with 5 ml water, and after removal of tetrahydrofuran under vacuum it was extracted with 3×120 ml ethyl acetate. The organic layer was washed with the mixture of water and brine, dried over sodium sulfate and evaporated to dryness. The crude product was purified by FLASH chromatography with hexane-ethyl acetate 1:3, to give 172 mg (46.5%) of the title compound. $[\alpha]_D^{25}$+67.5° (c 0.2, EtOH). UV max (EtOH): 258–259 nm (ε 11520). $^1$H-NMR (20:1, CDCl$_3$DMSO-d$_6$): δ0.73 (s, 3H, CH$_3$), 1.16 (d, 3H, J=6.7 Hz, CH$_3$), 1.34 (s, 6H, 2CH$_3$), 4.22 (brm, 1H, CH), 4.43 (brm, 1H, CH), 4.98 (s, 1H, CH of =CH—). 5.34–5.42 (m, 4H, CH of =CH$_2$, allene, =CH—), 6.14 (d, 1H, J=11 Hz, =CH—), 6.35 (d, 1H, J=11 Hz, =CH—).

EXAMPLE 8

[3aS-[3(1S*,2R*),3aα,7α,7aβ]]-3-[5-[[(1,1-dimethylethyl) dimethylsilyl]oxy]-1,5-dimethyl-4-(phenylsulfinyl)-2,3-hexadienyl]-3a,4,5,6,7,7a-hexahydro-3a-methyl-1H-inden-7-ol acetate To a solution of 681 mg (1.52 mmol) of [3aS-[3(1R*, 2R*), 3aα,7α,7aβ]]-7-acetyloxy)-α-[3[[(1,1-dimethylethyl) dimethylsilyl]oxy]-3-methyl-1-butynyl]-3a,4,5,6,7,7a-hexahydro-β,3a-dimethyl-1H-indene-3-ethanol in 40 ml anhydrous ether was added 0.423 ml (3.04 mmole) of triethylamine. To this stirred mixture at −78° C. was added dropwise freshly prepared phenyl sulfenyl chloride until yellow color persisted. After stirring for additional one hour, the reaction mixture was warmed to room temperature, diluted with water and extracted with ether. Ether extracts were washed with 2N potassium bicarbonate, water and brine, dried over sodium sulfate, and evaporated to dryness. The crude product was purified first by FLASH chromatography with ethyl acetate and then by HPLC with hexane-ethyl acetate 3:1 to give 655 mg (51%) of the title epimeric sulfoxides.

EXAMPLE 9

[3as-[3(1S*,2S*),3aα,7α,7aβ]]-3-[5-[[(1,1-Dimethylethyl) dimethylsilyl]oxy]-1,5-dimethyl-2,3-hexadienyl]-3a,4,5,6, 7,7a-hexahydro-3a-methyl-1H-inden-7-ol To the solution of 655 mg, (1.18 mmole) of [3aS-[3(1S*, 2R*), 3aα,7α,7aβ]]-3-[5-[[(1,1-dimethylethyl) dimethylsilyl]oxy]-1,5-dimethyl-4-(phenylsulfinyl)-2,3-hexadienyl]-3a,4,5,6,7,7a-hexahydro-3a-methyl-1H-inden-7-ol acetate in 200 ml anhydrous ether was added 0.176 ml (4.35 mmole) of anhydrous methanol. Thus obtained mixture was cooled to −100° C. in pentane-liquid nitrogen bath and 8 ml (14.1 mmole) of 1.7M tert.buthyl lithium was added dropwise, when the color turned brownish-yellow. TLC indicated that the reaction was complete. It was quenched with 4 ml methanol, washed with water to neutral, then with brine, dried over sodium sulfate and evaporated. The residue (730 mg) was dissolved in 8 ml ethanol and after addition of 4 ml 2N sodium hydroxide, it was heated at 70° C. for 1½ hours. After dilution with brine-water, it was extracted with ethyl acetate. The extract was washed with water until it was neutral. then with brine, dried over sodium sulfate and evaporated to dryness. The crude product (610 mg) was purified by HPLC with hexane-ethyl acetate 7:1 to give 208 mg (45.2% of the title compound; $[a]_D^{25}$10.82∞(c 0.5%, EtOH); $^1$H-NMR (CDCl$_3$): d 0.08 (s, CH, SiMe$_2$), 0.86 (s, 9H, Si-tButyl), 1.09 (s, 3H, CH$_3$), 1.13 (d, 3H J=6.9 Hz, CH$_3$), 1.99, 2.27 (m, 2H, CH$_2$), 2.83 (m, 1H, CH), 4.18 (brs, 1H, CH), 5.21 (t, 1H, J=6.4 Hz, =CH—), 5.34 (dd, 1H, J=2.7 and 6.4 Hz, =CH—), 5.44 (brs, 1H =C—).

EXAMPLE 10

[3aS-[3(1S*,2S*),3aa,7ab]]-3-[5-[[(1,1-Dimethylethyl) dimethylsilyl]oxy]-1,5-dimethyl-2,3-hexadienyl]-3-a,4,5,6, 7,7a-hexahydro-3a-methyl-1H-inden-7-one To the solution of 415 mg (1.06 mmole) of [3aS-[3(1S*, 2S*), 3aa,7a,7ab]]-3-[5-[[(1,1-dimethylethyl)dimethylsilyl] oxy]-1,5-dimethyl-2,3-hexadienyl]-3a,4,5,6,7,7a-hexahydro-3a-methyl-1H-inden-7-ol in 9 ml of anhydrous methylene chloride was treated with 1.2 g (3.19 mmole) of pyridinium dichromate and 60 mg of pyridinium p-toluenesulfonate. After stirring for 2 hours at room temperature, additional 564 mg (1.5 mmole) of pyridinium dichromate and 28 mg of pyridinium p-toluene sulfonate were added and the reaction mixture was stirred at room temperature for 2.5 hours longer. 25 ml of ether was then added, and after stirring for 20 minutes the mixture was filtered over celite and washed with ether (3×50 ml). The filtrate was washed with ice-cold cold 20 ml 1N HCl, water, 2N KHCO$_3$ (40 ml) and a mixture of water and brine. The aqueous layers were extracted with ethyl acetate. The combined organic layers were dried over sodium sulfate and evaporated to dryness. The crude product was purified by FLASH chromatography with hexane-ethyl acetate 15:1 to give 310 mg (75%) of the title compound.

EXAMPLE 11

1,25-Dihydroxy-16,22R,23-triene-cholecalciferol

To a solution of 755 mg (1.3 mmole) of [3S-(1Z,3α,5β] -2-[3,5-bis[[(1,1-dimethyl)dimethylsilyl]oxy]-2-methylene-cyclohexylidene]-ethyl]-diphenylphosphine oxide in 8 ml anhydrous tetrahydrofurane at −78° C. was added dropwise 0.79 ml (1.26 mmole) of 1.6M n-butyllithium in hexane under argon. After stirring for 5 minutes. to thus formed red solution was added a solution of 310 mg (0.8 mmole) of [3aS-[3(1S*,2S*),3aα,7aβ]]-3-[5-[[(1,1-dimethylethyl) dimethylsilyl]oxy]-1,5-dimethyl-2,3-hexadienyl]-3a,4,5,6, 7,7a-hexahydro-3a-methyl-1H-inden-7-one in 4 ml anhydrous tetrahydrofuran, dropwise over 10 minutes. The mixture was stirred under argon at −78° C. under argon for additional 90 minutes, and then quenched by addition of 10 ml of 1:1 mixture of 2N aqueous potassium sodium tartrate and 2N aqueous KHCO$_3$, and extracted with 3×120 ml ethylacetate. The organic phase was washed with brine, dried over sodium sulfate and evaporated to dryness. The crude trisylylated end product was purified by FLASH chromatography with hexane-ethyl acetate 40:1. The 434 mg of thus purified intermediate was dissolved in 5.5 ml of anhydrous tetrahydrofuran and treated with 9.96 ml of 1M tetrabutyl ammonium fluoride in tetrahydrofuran under argon by stirring for 71 hours at room temperature. After quenching with 5 ml water, tetrahydrofuran was removed under vacuum, the residue diluted with water and extracted with 3×120 ml ethyl acetate. The organic layer was washed with the mixture of water and brine, dried over sodium sulfate and evaporated to dryness. The crude product was purified by FLASH chromatography with hexane-ethyl acetate 1:3, to give 215 mg (65.5%) of the title compound, which crystallized from the mixture of tetrahydrofuran and methyl formate (1:7); m.p. 174–176∞C, $[\alpha]_D^{25}$+0∞(c 0.2, EtOH). UV max (EtOH): 264 nm (e 17080). $^1$H-NMR (CD$_3$OD): d 0.74 (s, 3H, CH$_3$), 1.18 (d, 3H, J=6.9 Hz, CH$_3$), 1.30 (s, 3H, CH$_3$), 1.31 (s,3H, CH$_3$), 1.31 (s, 3H, CH$_3$), 1.52 (m, 1H, CH of CH$_2$), 1.89 (t, 2H, J=5.6 Hz, CH$_2$), 4.13 (q, 1H, J=5.3 Hz, CH), 4.36 (t, 1H, J=5.8 Hz, CH), 5.21 (t, 1H, J=6.7 Hz, =CH—); 5.30 (s, 1H, CH of =CH$_2$), 5.33 (dd, 1H, J=2.3 and 6.2 Hz, =CH—), 5.45 (s, 1H, =CH—), 6.17 (d, 1H, J=11.2 Hz =CH—), 6.3 (d, 1H, J=11.2 Hz, =CH—).

EXAMPLE 12

Oral Dosage Form Soft Gelatin Capsule

|  | mg/capsule |
|---|---|
| 1.25-dihydroxy-16,22R,23-triene cholecalciferol (Compound A) | 0.005–0.050 |
| Butylated Hydroxytoluene (BHT) | 0.016 |
| BUtylated Hydroxyanisole (BHA) | 0.016 |
| Myglycol ® -812 qs | 160 |

1. Suspend BHT and BHA in Myglycol®-812. Warm to about 50° C. and stir until dissolved.
2. Dissolve Compound A in the solution from Step 1.
3. Fill the solution from Step 2 in a soft gelatin cap.

All steps performed under a nitrogen atmosphere and protected from light.

EXAMPLE 13

Oral Dosage Form Soft Gelatin Capsule

|  | mg/capsule |
|---|---|
| Compound A | 0.005–0.050 |
| α-Tocopherol | 0.016 |
| Myglycol ® -812 qs | 160 |

1. Suspend (α-Tocopherol in Myglycol®-812. Warm to about 50° C., and stir until dissolved.
2. Dissolve Compound A in the solution from Step 1.
3. Fill the solution from Step 2 in a soft gelatin cap.

All steps are performed under a nitrogen atmosphere and protected from light.

EXAMPLE 14

Topical Dosage Form Cream

|  | % w/w |
|---|---|
| Compound A | 0.00001–0.10 |
| Cetyl Alcohol | 1.50 |
| Stearyl Alcohol | 2.50 |
| Sorbitan Monostearate (Span 60) | 2.00 |
| Mineral Oil | 2.00 |
| Glyceryl Monostearate and Polyoxyethylene Glycol Stearate Blend (Arlacel 165) | 4.00 |
| Polysorbate 60 (Tween 60) | 1.00 |
| Caprylic/Capric Triglyceride | 5.00 |
| Sorbitol Solution | 4.00 |
| Edetate Disodium | 0.10 |
| Butylated Hydroxyanisole (BHA) | 0.02 |
| Sorbic Acid | 0.20 |
| Potassium Sorbate | 0.1–0.2 |
| Water q.s. to | 100.00 |

1. Stir Compound A until dissolved in caprylic/capric triglyceride.
2. Warm mixture of cetyl alcohol, stearyl alcohol, Span 60, mineral oil, Arlacel 165, Tween 60 and BHA to about 70°–75° C., to form oily solution.
3. Add solution from Step 1 to solution from Step 2 while mixing.
4. Warm mixture of water, sorbitol solution, edetate disodium, sorbic acid, and potassium sorbate to 70°–75° C.
5. Add solution from Step 3 to solution from Step 4 while emulsifying with a high speed mixer.
6. Cool emulsion from Step 5 to room temperature until emulsion conceals.

EXAMPLE 15

Topical Dosage Form Gel

|  | % w/w |
|---|---|
| Compound A | 0.00001–0.10 |
| Butylated Hydroxyanisole (BHA) | 0.02 |
| Hydroxypropyl Cellulose | 3.00 |
| Ethyl Alcohol, USP | 45.00 |
| Water q.s. to | 100.00 |

1. Dissolve BHA in mixture of ethyl alcohol and water.
2. Dissolve Compound A in solution from Step 1.
3. Disperse hydroxypropyl cellulose in solution from Step 2.

EXAMPLE 16

Topical Dosage Form Gel

|  | % w/w |
|---|---|
| Compound A | 0.00001–0.10 |
| Propylene Glycol | 10.00 |
| Caprylic/Capric Triglyceride | 30.00 |
| Butylated Hydroxyanisole (BHA) | 0.02 |
| Ethyl Alcohol, Absolute q.s. to | 100.00 |

1. Dissolve Compound A in ethyl alcohol.
2. Add BHA to solution from Step 1 and dissolve.
3. Add propylene glycol and caprylic/capric triglyceride to solution from Step 2 and mix until solution becomes clear.

We claim:

1. A compound of the formula

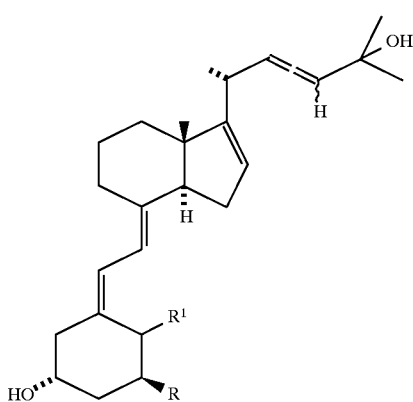

I wherein R is hydroxy and $R^1$ is $H_2$ or $=CH_2$ or R is hydrogen or fluoro and $R^1$ is $=CH_2$.

2. A compound in accordance with claim 1, wherein R is hydroxy.

3. A compound in accordance with claim 1, wherein $R^1$ is $=CH_2$.

4. A compound in accordance with claim 2, 1,25-dihydroxy-16,22R,23S-triene-cholecalciferol.

5. A compound in accordance with claim 2, 1,25-dihydroxy-16,22S,23,-triene-cholecalciferol.

6. A pharmaceutical composition comprising (a) an effective amount of a compound of the formula

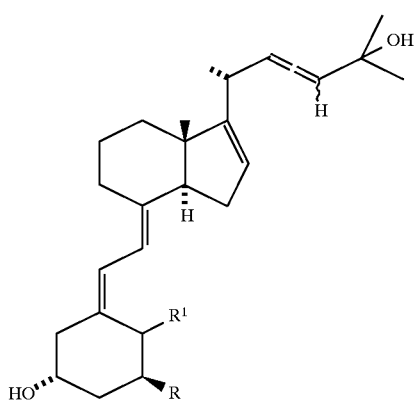

wherein R is hydroxy and $R^1$ is $H_2$ or $=CH_2$ or R is hydrogen or fluoro and $R^1$ is $=CH_2$ and (b) an inert carrier.

7. A pharmaceutical composition in accordance with claim 6, wherein the compound of formula I is 1,25-dihydroxy-16,22S,23-triene-cholecalciferol.

8. A pharmaceutical composition in accordance with claim 6, wherein the compound of formula I is 1,25-dihydroxy-16,22R,23-triene-cholecalciferol.

9. A compound of the formula

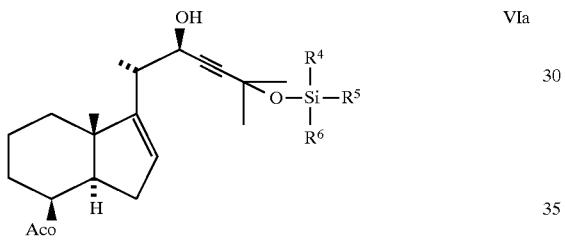

wherein $R^4$ and $R^6$ are independently lower alkyl and $R^5$ is independently lower alkyl, an aryl selected from the group consisting of an unsubstituted phenyl and a phenyl substituted by one or more lower alkyl groups, or an ar-lower alkyl selected from the group consisting of p-tolyl, benzyl, phenylethyl and phenylpropyl.

10. A compound of the formula

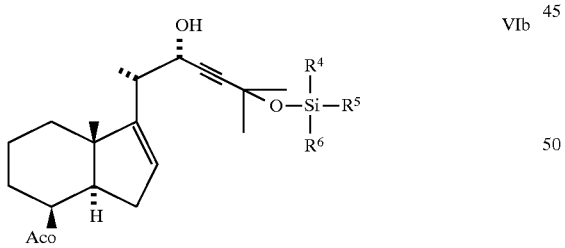

wherein $R^4$ and $R^6$ are independently lower alkyl and $R^5$ is independently lower alkyl, an aryl selected from the group consisting of an unsubstituted phenyl and a phenyl substituted by one or more lower alkyl groups, or an ar-lower alkyl selected from the group consisting of p-tolyl, benzyl, phenylethyl and phenylpropyl.

11. A compound of the formula

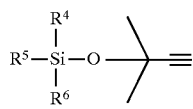

wherein $R^4$ and $R^6$ are independently lower alkyl and $R^5$ is independently lower alkyl, an aryl selected from the group consisting of an unsubstituted phenyl and a phenyl substituted by one or more lower alkyl groups, or an ar-lower alkyl selected from the group consisting of p-tolyl, benzyl, phenylethyl and phenylpropyl.

12. A compound of the formula

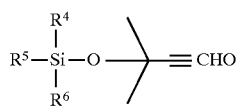

wherein $R^4$ and $R^6$ are independently lower alkyl and $R^5$ is independently lower alkyl, an aryl selected from the group consisting of an unsubstituted phenyl and a phenyl substituted by one or more lower alkyl groups, or an ar-lower alkyl selected from the group consisting of p-tolyl, benzyl, phenylethyl and phenylpropyl.

13. A compound of the formula

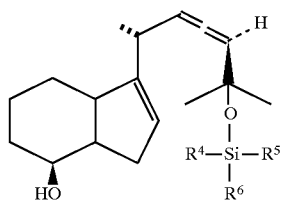

wherein $R^4$ and $R^6$ are independently lower alkyl and $R^5$ is independently lower alkyl, an aryl selected from the group consisting of an unsubstituted phenyl and a phenyl substituted by one or more lower alkyl groups, or an ar-lower alkyl selected from the group consisting of p-tolyl, benzyl, phenylethyl and phenylpropyl.

14. A compound of the formula

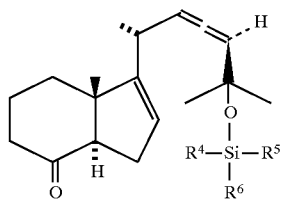

wherein $R^4$ and $R^6$ are independently lower alkyl and $R^5$ is independently lower alkyl, an aryl selected from the group consisting of an unsubstituted phenyl and a phenyl substituted by one or more lower alkyl groups, or an ar-lower alkyl selected from the group consisting of p-tolyl, benzyl, phenylethyl and phenylpropyl.

15. A compound of the formula

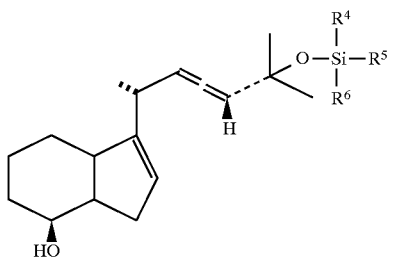

wherein $R^4$ and $R^6$ are independently lower alkyl and $R^5$ is independently lower alkyl, an aryl selected from the group consisting of an unsubstituted phenyl and a phenyl substituted by one or more lower alkyl groups, or an ar-lower alkyl selected from the group consisting of p-tolyl, benzyl, phenylethyl and phenylpropyl.

16. A compound of the formula

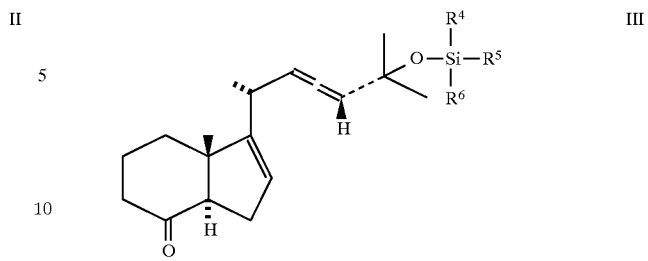

wherein $R^4$ and $R^6$ are independently lower alkyl and $R^5$ is independently lower alkyl, an aryl selected from the group consisting of an unsubstituted phenyl and a phenyl substituted by one or more lower alkyl groups, or an ar-lower alkyl selected from the group consisting of p-tolyl, benzyl, phenylethyl and phenylpropyl.

* * * * *